United States Patent [19]

Smith et al.

[11] Patent Number: 4,780,333
[45] Date of Patent: Oct. 25, 1988

[54] METHOD FOR TREATMENT OF AIR CONDITIONING SYSTEM

[75] Inventors: Calvin G. Smith, Dearborn; Lee Carrick, Jr., Grosse Point, both of Mich.

[73] Assignee: Ford Motor Company, Dearborn, Mich.

[21] Appl. No.: 947,063

[22] Filed: Dec. 29, 1986

[51] Int. Cl.⁴ ............................ B65D 7/22; F24F 3/16
[52] U.S. Cl. .......................................... 427/236; 62/78; 427/239; 427/318; 427/327; 427/409; 427/412
[58] Field of Search .............. 427/236, 239, 318, 409, 427/421, 327; 62/78

[56] References Cited

U.S. PATENT DOCUMENTS 2,902,834  9/1959  Bosworth et al. ...................... 62/78
3,591,328  7/1971  Szappanyos et al. ................ 427/236
4,084,747  4/1978  Alliger .................................. 239/4

Primary Examiner—Janyce Bell
Attorney, Agent, or Firm—Peter D. McDermott; Roger L. May

[57] ABSTRACT

A method is provided of treating an air-contacted surface of an air conditioning system comprising the steps of:

(A) introducing to the air passage and air-borne biocide in a biocidally effective amount; and
(B) subsequently introducing into the air passage an air-borne biostat adapted to coat the surface with an air-driable, substantially water insoluble biostat coating, the biostat being introduced in an amount sufficient to coat the surface with a biostatically effective coating. According to another aspect of the invention, a kit is provided of interrelated parts for carrying out such treatment method.

15 Claims, No Drawings

METHOD FOR TREATMENT OF AIR CONDITIONING SYSTEM

The present invention is directed to a method of treating the air-contacted surfaces of an air conditioning system to deodorize such system and to reduce certain microbial growth therein.

It has long been recognized that the air-contacted surfaces of an air conditioning system provide a substrate for microbial growth. As used herein, the term "air-contacted surfaces" of an air conditioning system means those surfaces within the air conditioning system which come in contact with the air being treated by the system. Thus, the air-contacted surfaces include, for example, the inside surfaces of the air ducts, the surfaces of the evaporator core, vent surfaces, blower motor surfaces, etc. Bacteria and fungi are known to grow in such air ducts, on the evaporator core and on the sealants, vent closure panels, etc. of air conditioning systems The presence of condensed moisture on these surfaces, especially at elevated temperatures such as when the system is turned off after being operated for a period, allows bacteria and fungi to multiply. When the system is next operated, such bacteria, fungi and their metabolic products are carried by the air which is being moved through the system and, thus, are introduced into the area which is being air conditioned. This can cause the treated air to have an offensive odor. Also, certain people are believed to have adverse reactions to such micro- organisms, their symptoms possibly including allergic rhinitis, bronchial asthma, and other minor respiratory ailments. This problem can be particularly troublesome for those persons who rely on an air conditioning system to help control such symptoms by filtering in-coming air and/or by recirculating air to reduce the pollen and spore content thereof.

This problem can be particularly noticable in automobiles, where air conditioning systems introduce treated air into a passenger compartment of relatively small volume. If the air conditioning system has been contaminated by bacteria, fungi or the like, any objectionable odor or air-borne respiratory irritants will be relatively concentrated. Also, because a vehicle air conditioning system typically is operated intermittently, the warm moist conditions for microbial growth are repeatly renewed. An investigation into the relationship between automobile air-conditioners and respiratory allergies was documented by P. Kumar, M.D., et al, "Respiratory Allergies Related To Automobile Air Conditioners"; *N. Engl. J. Med.;* 1981; 311; 1619-21. Kumar et al conclude by recommending an inquiry into the exacerbation of respiratory ailment symptome in association with autpmobile air conditioning to determine whether decontamination of the system or other control measures would be effective.

In that regard, methods have long been proposed for treating the air-contacted surfaces of air conditioning systems to deodorize tham and to prevent the dissemination of fungal spores which cause irritation in susceptible individuals. In U.S. Pat. No. 3,591,328 to Szappanyos et al, one such method is proposed which comprises applying a fungicidal film to such surfaces. Specifically, Szappanyos et al suggest introducing into the air inlet of an air conditioning system an admixture of a fungistat/fungicide, a film-reinforcing material and an air driable solvent. The air-contacted surfaces are coated and the solvent then evaporates, leaving a fungal growth inhibiting film or coating. This method has been found to be of limited effectiveness, or to be effective for insufficient duration, however, particularly for treatment of systems which are already contaminated. Thus, the Szappanyos et al method has been found to be inadequate, for example, for treatment of an automobile air conditioning system which is identified as requiring treatment to remove an objectionable odor, since such system already is contaminated. While not wishing to be bound by theory, it is believed that the anti-fungal film may not adequately form on or adhere to contaminated surfaces or that contaminants other than fungi may be involved. Presently, work is being done regarding the addition of anti-microbial agents to adhesives, sealants, plastics, and other materials used in air conditioning systems. Many existing systems, however, do not have such self-protected materials. Moreover, the antimicrobial efficacy of these materials can be lost over time.

It is an object of the present invention to provide a method of treating an air conditioning system which is effective to decontaminate and deodorize the same for an extended period of time, even through repeated on/off cycling of the system. It is a particular object of the invention to provide such a treatment method which can be effective even without disassembly of the air conditioning system and separate treatment of the system components.

These and additional objects of the invention will be understood from the following disclosure.

SUMMARY OF THE INVENTION

According to the present invention a method is provided of treating an air-contacted surface of an air passage of an air conditioning system, which method comprises the steps of:

(A) introducing biocide into the air passage as a directed air-borne mist in a biocidally effective amount; and (B) subsequently introducing biostat into the air passage as a directed air-borne mist, which biostat is adapted to coat the surface of the air passage with an air-driable, substantially water insoluble biostat coating, the biostatic being introduced in an amount sufficient to coat the surface with a biostatically effective coating. As used in this disclosure, the term "directed air-borne mist" is intended to include a mist, fog or spray of a liquid composition which has been atomized or nebulized by the flow of pressurized air through a nozzle, etc.

According to another aspect of the present invention, a kit of interrelated parts for carrying out the aforesaid method of treating an air conditioning system is provided. Specifically, the air conditioning system treatment kit is adapted to provide a preferred embodiment of the method of the invention and comprises interrelated parts capable of being used in conjunction with a source of pressurized air. More specifically, the kit comprises:

(A) a first container containing a treatmenteffective quantity of a liquid biocide activating agent comprising a substantially water soluble acid component selected from the group consisting of organic acids and mixtures thereof with inorganic acid, the acid component comprising at least about 15% by weight lactic acid;

(B) a second container containing a treatmenteffective quantity of a liquid biocide comprising a $ClO_2$ liberating material, wherein one of such first container and such second container is of sufficient volume to contain the entire liquid contents of both containers; and (C) a third container containing a treatmenteffective quantity of a film-forming liquid biostat.

Optionally, the kit also comprises a spray nozzle having an outlet and a first supply passage adapted to supply pressurized air to the nozzle outlet and a second supply passage adapted to supply a liquid treatment agent (i.e., the biocide and the biostat) to the nozzle outlet, the nozzle being adapted to release the treatment agent from the nozzle outlet as a directed air-borne mist.

As will be understood from the foregoing disclosure, the treatment method of the present invention involves application of a biocide followed by application of a biostat, each of these agents being introduced into the air conditioning system as an air-borne mist. This method offers a significant advantage in that the air conditioning system typically need not be substantially disassembled to achieve substantially complete coverage of the air ducts, evaporator core, and other aircontacted surfaces thereof. While not wishing to be bound by theory, it presently is understood that by first treating the air-contacted surfaces with a biocide, the air conditioning system is substantially decontaminated. That is, those bacteria and fungi which cause a disagreeable odor in the treated air or which cause an allergic or other adverse reaction in susceptible individuals are killed. Subsequently, good coverage and film adhesion can be obtained upon introduction of the film-forming biostat, which will inhibit re-contamination of the decontaminated surfaces. Thus, the treatment method of the present invention is effective for treatment of systems which already have been contaminated and, furthermore, provides longlasting microbial inhibition in the system.

DETAILED DESCRIPTION OF PREFERRED EMBODIMENTS

As disclosed above, the method of the present invention involves introducing into an air passage of an air conditioning system an air-borne biocide. It has been found that to successfully treat an air conditioning system for objectionable odors caused by bacteria and/or fungi, it is necessary to decontaminate the system by the application of biocide prior to the application of a biostat which then inhibits re-contamination for a prolonged period. As used herein, the term biocide means any antimicrovial agent which is effective at atmospheric temperatures and conditions destroy bacteria and/or fungi present on an air-contacted surface within an air passage of an air conditioning syste, which bacteria or fungi cause either an objectionable odor in the air treated by the air conditioning system or release into such treated air fungal spores or other microbial organisms or metabolic products which are an irritant or allergen to susceptible individuals. Thus, suitable biocides for this invention include certain substances or mixtures of substamces meeting the definition of one or more types of anti-microbial agents defined in the regulations of the Environmental Protection Agency (40 U. S. C. ∫ 162.3(ff) (2) (i) (A,B,D-F). Specifically, biocide as used herein includes certain "disinfectants" which destroy or irreversably inactivate infections or other undesireable bacteria ot pathegenic fungi on surfaces of inanimate objects. Also included are certain "sanitizers" which reduce the number of living bacteria on inanimate surfaces in water, or in air. Also included are certain "sterilizers" which destry all bacteria, fungi and their spores on inamimate surfaces. Also included are certain fungicides which destroy fungi (including yeasts) on inanimate surfaces. Also included are certain "commodity preservatives" which destroy bacteria on materials such as adhesives and plastics. Of course, it is recognized that the definition of any of these terms pursuant to government regulation may change from time to time and the term biocide as used herein is not intended to be limited to that provided by any government regulatory agency definition.

The biocides of the present invention can be packaged and dispensed as a liquid. Numerous suitable biocides are known to the skilled of the art, including many which are commercially available such as, for example, formaldehyde, ethylene oxide, gluteraldehyde, and quaternary ammonium compounds. Additional suitable biocides will be apparent to the skilled of the art in view of the present disclosure. A preferred group of biocides is that disclosed in U.S. pat. No. 4,084,747 to Alliger (reissued as No. RE. 31,779), the disclosure of which is incorporated herein by reference. The Alliger patent discloses a biocide composition produced by contacting a $ClO_2$ liberating material and a substantially water soluble acid component selected from the group consisting of organic acids and mixtures thereof with inorganic acid, the acid component comprising at least about 15% by weight lactic acid. The acid material is contacted with the $ClO_2$ liberating material, preferably with sodium chlorite, in aqueous media, the amount of acid being sufficient to lower the pH of the aqueous media to less than about 7. This composition is a $ClO_2$ liberating material. That is, the sodium chlorite, in contact with the water soluble acid component liberates $ClO_2$. Although sodium chlorite is most preferred, other water-soluble chlorites can be used and will be apparent to the skilled of the art in view of this disclosure. preferably the acid component consists essentially of lactic acid.

The method of the present invention further comprises introducing into the air passage of an air conditioning system an air-borne biostat. As used herein, the term "biostat" means any anti-microbial agent which inhibits or prevents the growth on an air-contacted surface of an air conditioning system of bacteria and/or fungi which cause an objectionable odor in air treated by the air conditioning system or which release fungal spores or other microbial organisms which are an irritant or allergens to susceptible individuals. Thus, while certain biocides may be effective also as a biostat, as used herein, other materials ineffective to kill bacteria or fungi and thus not qualifying as biocides may, nevertheless, be effective to inhibit their growth and thus be within the meaning of the term biostat as used herein. Accordingly, in addition to certain of the antimicrobial agents discussed above, the biostat of the present invention includes substances or mixtures of substances which qualify as bacteriastats and/or fungistats, as those terms are currently defined by the Environmental protection Agency (40 U.S.C. §162.3(ff) (2)(i)(C,E). Specifically, the term biostat would include, but not necessarily be limited to, "bacteriastats" which inhibit the growth of bacteria in the presence of moisture and "fungistats" which inhibit the growth of fungi (including yeasts) on inanimate surfaces. The meaning of the term biostat, however, as used herein, is not limited to the definition of any term provided by government regulatory agency. Numerous suitable biostats are known to the skilled of the art, including many of which are commercially available, including, for example, diiodomethyl p-tolyl sulfone, 2-(4-thiazoyl)-benzimidazole, and 10,10′-oxybisphenozarsine. Additional suitable biostats will be apparent to the skilled of the art in view of the present disclosure.

As hereinbefore explained, the present invention provides the application of a substantially waterinsoluble biostatically-effective film to the aircontacted surfaces of an air conditioning system, which film acts as a biostat, that is, has biostat properties (effective at the temperatures and the atmospheric conditions likely to be encountered by the air-contacted surfaces of the air conditioning system) sufficient to prevent or substantially inhibit the growth or multiplication of fungi, bacteria and other microbial organisms which cause an offensive odor in the air treated by the air conditioning system or which release irritants or allegens into such air. The biostat film may consist essentially of a biostat material which itself is sufficiently film-forming. Alternatively, the biostat film may comprise a biostatically active material in conjunction with a film-reinforcing material in an air-driable solvent. In either case, the biostat material should have low water solubility to prevent the rapid removal thereof from the air-contacted surfaces of the air conditioning system due to water condensation thereon and the gravity flow of water thereover during and immediately after operation of the air conditioning system. In addition, the biostat should be relatively non-volatile at the temperatures experienced in the operation of the air conditioning system. Finally, the biostat of the present invention can be packaged and dispensed as a liquid. Where a biostatically effective material is used in conjunction with a film-reinforcing material, the biostat and film-reinforcing material should be soluble in a common solvent which is air volatile at substantially ambient temperatures. Finally, the biostat (whether alone or in conjunction with a film-reinforcing agent), in accordance with the method of the present invention, should be depositable as a substantially non-tacky film from an air-borne mist.

Where a film-reinforcing material is employed together with a biostat material to form the biostat coating, the film-reinforcing material should be soluble, as noted above, in a solvent common to the biostat. It should be sufficiently non-flamable at the temperatures encountered in the air conditioning system. Of course, it must be capable of drying in air to form a dry film which is not significantly pressure sensitive or tacky. As mentioned above, once the film has dried it should have low water solubility. Finally, the film should not significantly block or streamline the flow of air through the heat exchanger portion of the air conditioning system, as this could undesirably reduce the efficiency of the air conditioning system. Preferred film-reinforcing ingredients include the solvent-soluble phenol- formaldehyde resins available in solid form. One such resin is a rosin-modified maleic resin commercially available from Union Carbide Corporation under the trademark Unirez 7204.

Suitable solvents for phenol-formaldehyde resins, which of course must be selected also on their ability to dissolve the biostat material, preferably are selected from those which evaporate completely at atmospheric conditions. Such solvents include, for example, isopropyl alcohol, ethyl alcohol, butyl alcohol, methyl ethyl ketone and acetone. For use while an air conditioning system is in operation, 1,1,1-trichloroethane is preferred in view of its low flamability.

According to a preferred embodiment of the invention, the biostat comprises an admixture of a fungistat and an air-driable solvent having film reinforcing ingredients therein to coat the treated surface and to dry thereon to form a fungal growth inhibiting coating thereon. One preferred such composition is disclosed in the above discussed U.S. patent 3,591,328 to Szappanyos et al, the disclosure of which is incorporated herein by reference. The Szoppanyos et al patent discloses, for example, a film-forming composition comprising the fungicide dichlorophene, i.e., 2,2′-methylenebis-(4-chlorophenol) or bis(5-chloro-2-hydroxyphenyl)methane, together with phenol-formaldehyde resin in a solvent such as those disclosed above.

As previously mentioned, the biocide and then biostat materials of the present invention are applied by means of pressurized air, in atmospheric conditions, as an airborne nebulized or atomized liquid - that is, as a mist, fog or spray or the like. Generally it will be required to have the air conditioning system operating such that the biocide and biostat are suspended and carried in the form of liquid droplets in the air stream flowing through the air conditioning system. These droplets are deposited upon the walls of the air ducts and the air-contacted surfaces of the operative components of the air conditioning system. Care should be taken that there are no occupants in the motor vehicle or other space receiving the outflow of air from the air conditioning system to avoid unnecessary exposure to the biocide and biostat materials. Obviously, it will be advantageous to promote the flow of air through the air conditioning system by opening the windows of the automobile passenger compartment or of the enclosed space to which the treated air is being supplied.

Generally it will be preferred that the application of the biocide and biostat be made at a time when the air-contacted surfaces of the air conditioning system are dry. Thus, it is generally preferable to operate the air conditioning system, without refrigeration, by merely passing air through the system for a period of time sufficient to ensure dryness of these surfaces. Thereafter, the biocide material is introduced into the air stream flowing through the airhandling system, ideally in sufficient quantity and for a sufficient period of time to ensure deposit of a biocidally effective amount of such biocide material onto substantially all of the air-contacted surfaces of the air conditioning system. For this purpose it may be required to introduce the biocide (under the force of the pressurized air) into the outlet vents of the air conditioning system. Of course, the flow of air through the air conditioning system should be stopped or reduced to a minimum prior to introducing the biocide into the outlet vents. The air conditioning system blower should then be turned to its highest setting. The biocide is then sprayed into the air inlet. After a sufficient amount of the composition has been introduced into the air conditioning system, its introduction is terminated, but the flow of air through the system is continued, preferably, until such time as the air-contacted surfaces are again substantially dry. Subsequently, the film-forming biostat is introduced in the same manner as described above for the biocide material. Thereafter, the system is again operated to cause a flow of air therethrough to dry the biostatic film.

It has been found that the treatment method of the present invention is effective to deodorize and inhibit microbial growth within a motor vehicle or residential air conditioning system for a prolonged period of time, regardless of whether the air conditioning system was contaminated prior to receiving such treatment. Typically, for example, a motor vehicle air conditioning system so treated will remain odor free and substantially non-contaminated during use of the system throughout the course of a summer season.

As mentioned above, the biocide and biostat are introduced into the air conditioning system by means of pressurized air. Suitable equipment for this purpose is commercially available and will be apparent to those skilled in the art in view of the present disclosure. As used herein, the term pressurized air means any pressurized gas. Thus, for example, it is within the scope of the invention that either the biocide, the biostat or both be introduced into an air conditioning system as a directed mist from an aerosol can. Preferably, the equipment comprises a nozzle or spray gun adapted to receive the biocide and biostat as a liquid feed, to receive pressurized air feed from an external source and to combine the two feeds such that the biocide or biostat is sufficiently atomized or nebulized to remain as an air-borne mist while being carried on the flow of air through the air conditioning system to the air-contacted surfaces to be treated. Obviously, the outlet end of the spray gun or nozzle must be of a configuration and size which facilitates access to the air inlet and outlet openings of the air conditioning system. While the choice of equipment will depend, in part, upon the particular type of air conditioning system to be treated and upon such other factors as the choice of biocide and biostat materials and the expected operating conditions, various potentially suitable equipment will be readily apparent in view of the present disclosure. Thus, for example, a so-called "siphon spray blo-gun" with a siphon feed attachment is available from Milton Industries, Chicago, Illinois. Also potentially suitable are various spray guns, with or without extension nozzles such as a combination gravity feed/siphon feed spray gun with extension nozzle available from Binks Manufacturing, Chicago, Illinois. According to one preferred embodiment of the invention, the delivery equipment comprises a siphon feed spray head assembly with remote solution container available from Dirkes Industries, Warren, Michigan. Specifically, Dirkes spray unit No. 3366 is found to perform well with the preferred biocides and biostats disclosed above. Thus, the delivery system preferably comprises the aforesaid Dirkes spray unit in combination with a source of high pressure air. The Dirkes spray unit comprises (i) a spray nozzle, (ii) a high pressure air hose to the spray nozzle, (iii) an air pressure regulator mediate the source of high pressure air and the high pressure air hose, (iv) a manually operated on/off air control valve in the air pressure hose mediate the air pressure regulator and the spray nozzle, (v) a remote container adapted to feed the biocide and subsequently the biostat to the spray nozzle, and (vi) a feed hose from the container to the spray nozzle. The air control valve preferably is of the spring loaded toggle type, wherein moving the toggle forward or rearward a small degree will open the valve and moving the toggle further in either direction will cause it to lock in the open position. The toggle then can be deflected back to the center position to close the valve.

The following is a description of a preferred embodiment of the invention adapted for treating motor vehicle air conditioning systems. As a preliminary step, all air conditioning system condensate drains should be checked for obstructions. If any are obstructed, they should be repaired before proceeding. Then, with the vehicle engine turned off, the air conditioning clutch is disconnected from the electrical circuit. Typically, it will be necessary to operate the vehicle's engine throughout this procedure to prevent excessive battery drain and to provide a source of vacuum required by some air conditioning control systems. Of course, before application of the biocide or biostat, care must be taken to follow all prescribed precautionary measures, such as wearing safety goggles and a suitable respiratora etc. to avoid contact with the biocide and biostat. According to this embodiment, the biocide consists of a sodium chlorite solution, available from Alcide Corporation, Norwalk, Connecticut under the brand name Exspor Base (4:1:1), EPA Registration No. 45631-03, and a separately packaged organic acid activator available from Alcide Corporation under the brand name Exspor Activator (4:1:1), EPA Registration No. 45631-03. The sodium chlorite solution and the activator are used in a volume ratio of 1:4, respectively, the activator having been pre-diluted with water in a ratio of one (1) part activator to four (4) parts water. Preferably, the container holding the activator is sufficiently oversized to accept the sodium chlorite solution. Thus, to prepare the biocide for use, the sodium chlorite solution is added to the activator container and gently mixed. The biocide material then is poured into the fluid container of the Dirkes Industries' spray unit, model No. 3366, described above. The spray unit is connected to an air supply with a pressure regulator set between about 40 and 45 psi. preferably, the air-contacted surfaces of the air conditioning system have been thoroughly dried by operating the system to cause the flow of air therethrough. The biocide solution is applied to all parts of the air conditioning system, the bulk being directed to the evaporator core. To begin spraying, the on/off toggle of the air control valve is moved to the on position. The biocide can first be introduced into each of the outlet vents of the system including, for example, each defroster vent, side window demister vent, each panel register, and floor duct opening for a period of about from 5 to 10 seconds per opening. As the biocide is being blown into the system outlets, the system blower should be either off or set at its lowest setting. In a typical motor vehicle air conditioning system, this portion of the procedure should be performed with the system set for panel airflow, repeated with the system set for floor airflow, and repeated again with the system set for defrost airflow. Subsequently, the remainder of the biocide is introduced into the system inlets with the blower set for maximum airflow. Following the application of the biocide, the air conditioning system is thoroughly dried. Normally, a 30 minute drying period is sufficient if the system is operated to blow air therethrough (again, without refrigeration to speed drying of the air-contacted surfaces). When the ambient conditions are espectically humid, (e.g., relative humidity levels in excess of 70%) a hot-air gun or the like can be used to preheat the air entering the air conditioning system. The spray nozzle, fluid container and feed hose should be cleaned with a solvent such as isopropyl alcohol or the like to remove any residual biocide. When the air conditioning system is thoroughly dried, the biostat material is added to the fluid container of the spray unit. According to this preferred embodiment, the biostatic material is REP-66 Mold preventative, EPA Registration No. 35951-1 available from Condition-Air Co., Inc., Birmingham, Michigan. This material consists essentially of dichlorophene, 1,1,1-trichloroethane, 1-methyl-2-pyrrolidone, with rosin-modified maleic resin and film reinforcing material. The supply pressure regulator is again set at about from 40 to 45 psi and the spray procedure used for biocide is repeated for the biostat (except that spray duration for the outlets is about 1-5 seconds for each opening). The spray equipment should then be cleaned for subsequent use. The air conditioning system should not be operated in the refrigeration mode until the biostat film has completely dried. Normally 24 hours is a sufficient period of time. During this time the air conditioning system can be operated such as to cause a flow of air through the system for ventilation purposes only.

From the foregoing it will be appreciated that the present invention provides a novel method of treating an air conditioning system to deodorize and decontaminate the same. Further, the method can be applied typically without requiring disassembly of the system.

While an exemplary method of the invention has been described in detail, it will be apparent to those skilled in the art that the disclosed method may be modified. Therefore, the foregoing description is to be considered exemplary rather than limiting, and the full scope of the invention is intended to be covered by the following claims.

We claim:

1. A method of treating an air-contacted surface within an air passage of an air conditioning system, said method comprising the steps of:
   (A) introducing biocide into said air passage as a directed air-borne mist in a biocidally effective amount; and
   (B) subsequently introducing biostat into said air passage as a directed air-borne mist, said biostat being adapted to coat said surface with an air-driable, substantially water-insoluble biostat coating, said biostat being introduced in an amount sufficient to coat said surface with a biostatically effective coating.

2. The method of claim 1, wherein said biocide consists essentially of an aqueous composition of pH less than about 7 comprising (i) a ClO$_2$ liberating material and (ii) a substantially water soluble acid component selected from the group consisting of organic acids and mixtures thereof with inorganic acid, said acid component comprising at least about 15% by weight lactic acid.

3. The method of claim 1, wherein said biocide consists essentially of an aqueous composition of pH less than about 7 comprising (i) a water-soluble chlorite and (ii) a substantially water-soluble acid component selected from the group consisting of organic acids and mixtures thereof with inorganic acid, said acid component comprising at least about 15% by weight lactic acid.

4. The method of claim 1, wherein said biocide consists essentially of an aqueous composition of pH less than about 7 comprising (i) sodium chlorite and (ii) a substantially water-soluble acid component selected from the group consisting of organic acids and mixtures thereof with inorganic acid, said acid component comprising at least about 15% by weight lactic acid.

5. The method of claim 4, wherein said acid component consists essentially of lactic acid.

6. The method of claim 1, wherein said biocide consists essentially of formalehyde.

7. The method of claim 1, wherein said biostat comprises a fungicide substantially insoluble in water, a film re-inforcing material and a solvent effective to solubilize both said fungicide and said film forming material and which is volatile at atmospheric conditions.

8. The method of claim 7, wherein said fungicide consists essentially of 2,2'-methylenebis(4chlorophenol).

9. The method of claim 7, wherein said fungicide consists essentially of bis(5-chloro-2-hydroxyphenyl)methane.

10. The method of claim 7, wherein said film re-inforcing material consists essentially of phenolformaldehyde resin.

11. The method of claim 7, wherein said solvent is selected from the group consisting of ethyl alcohol, butyl alcohol, isopropyl alcohol, methyl ethyl ketone, acetone, and 1,1,1-trichloroethane.

12. The method of claim 1, wherein said biocide and said biostat each is introduced into said air passage by directed discharge from pressurized aerosol containers.

13. The method of claim 1, wherein said biocide and said biostat each is introduced into said air passage by directed discharge from a spray nozzle having an external source of pressurized air.

14. The method of claim 1 further comprising the preliminary step of substantially drying said air-contacted surface prior to introducing said biocide.

15. A method for treating the air-contacted surface of an air passage of an air conditioning system, said process comprising the steps of:
   (A) substantially drying said air-contacted surface;
   (B) subsequently introducing biocide into said air passage as a directed air-borne mist of an aqueous composition of pH less than about 7 comprising (i) sodium chlorite and (ii) a substantially water-soluble acid component selected from the group consisting of organic acids and mixtures thereof with inorganic acid, said acid component comprising at least about 15% by weight lactic acid;
   (C) again substantially drying said air-contacted surface;
   (D) subsequently forming a biostatic film on said air-contacted surface by introducing into said passage an air-borne mist of an admixture of dichlorophene and an air driable film reinforcing material in a volatile solvent; and
   (E) subsequently substantially drying said biostatic film.

* * * * *